United States Patent [19]

Katinger et al.

[11] 4,311,798

[45] * Jan. 19, 1982

[54] METHOD OF AND AN ARRANGEMENT FOR CULTIVATING CELLS OF ANIMAL AND HUMAN TISSUES

[75] Inventors: Hermann Katinger, Vienna; Winfried Scheirer, Wiener-Neudorf, both of Austria

[73] Assignee: Chemap AG, Maennedorf, Switzerland

[*] Notice: The portion of the term of this patent subsequent to Nov. 6, 1996, has been disclaimed.

[21] Appl. No.: 15,282

[22] Filed: Feb. 26, 1979

Related U.S. Application Data

[60] Continuation of Ser. No. 840,165, Oct. 6, 1977, Pat. No. 4,173,516, which is a division of Ser. No. 814,415, Jul. 11, 1977, abandoned.

[30] Foreign Application Priority Data

Jul. 15, 1976 [AT] Austria ................................ 5213/76

[51] Int. Cl.$^3$ ............................................... C12M 3/02
[52] U.S. Cl. ...................................... 435/286; 261/77; 435/284; 435/314; 435/313; 435/240; 435/241; 435/818
[58] Field of Search ............... 435/284, 286, 314, 240, 435/241, 313, 315, 316, 818; 261/77

[56] References Cited

U.S. PATENT DOCUMENTS

| | | | |
|---|---|---|---|
| 642,460 | 1/1900 | Kersten | 261/77 X |
| 3,476,366 | 11/1969 | Brooks et al. | 435/314 X |
| 3,681,200 | 8/1972 | Ridgway, Jr. | 435/314 |
| 3,705,082 | 12/1972 | Hondermarck et al. | 435/316 |
| 3,717,552 | 2/1973 | Hondermarck et al. | 435/314 |
| 3,790,141 | 2/1974 | Champeau | 261/77 |
| 3,880,716 | 4/1975 | Engelbart et al. | 435/818 X |
| 3,910,826 | 10/1975 | Kataoka | 261/77 X |
| 3,986,934 | 10/1976 | Müller | 435/314 |
| 4,017,565 | 4/1977 | Müller | 435/314 X |
| 4,036,699 | 7/1977 | Quigg | 435/314 |
| 4,173,516 | 11/1979 | Katinger et al. | 435/286 |

*Primary Examiner*—Robert J. Warden
*Attorney, Agent, or Firm*—Michael J. Striker

[57] ABSTRACT

A method of cultivating cells of animal and human tissues includes the steps of introducing the cells into a nutrient solution in which they tend to settle, and maintaining the cells in the solution in a suspended state so as to prevent their settling by introducing an oxygen-containing gas to the solution. An apparatus for carrying out the method includes a container for a nutrient solution, an arrangement for introducing the oxygen-containing gas into the container, and a guide arrangement in the container and operative for guiding the nutrient solution so that the latter performs a circulatory movement in the container when the oxygen-containing gas is introduced into the latter. The guide arrangement may be formed as a tubular member, as a substantially flat partition wall, or as an inner wall of a circumferentially complete tubular container.

16 Claims, 6 Drawing Figures

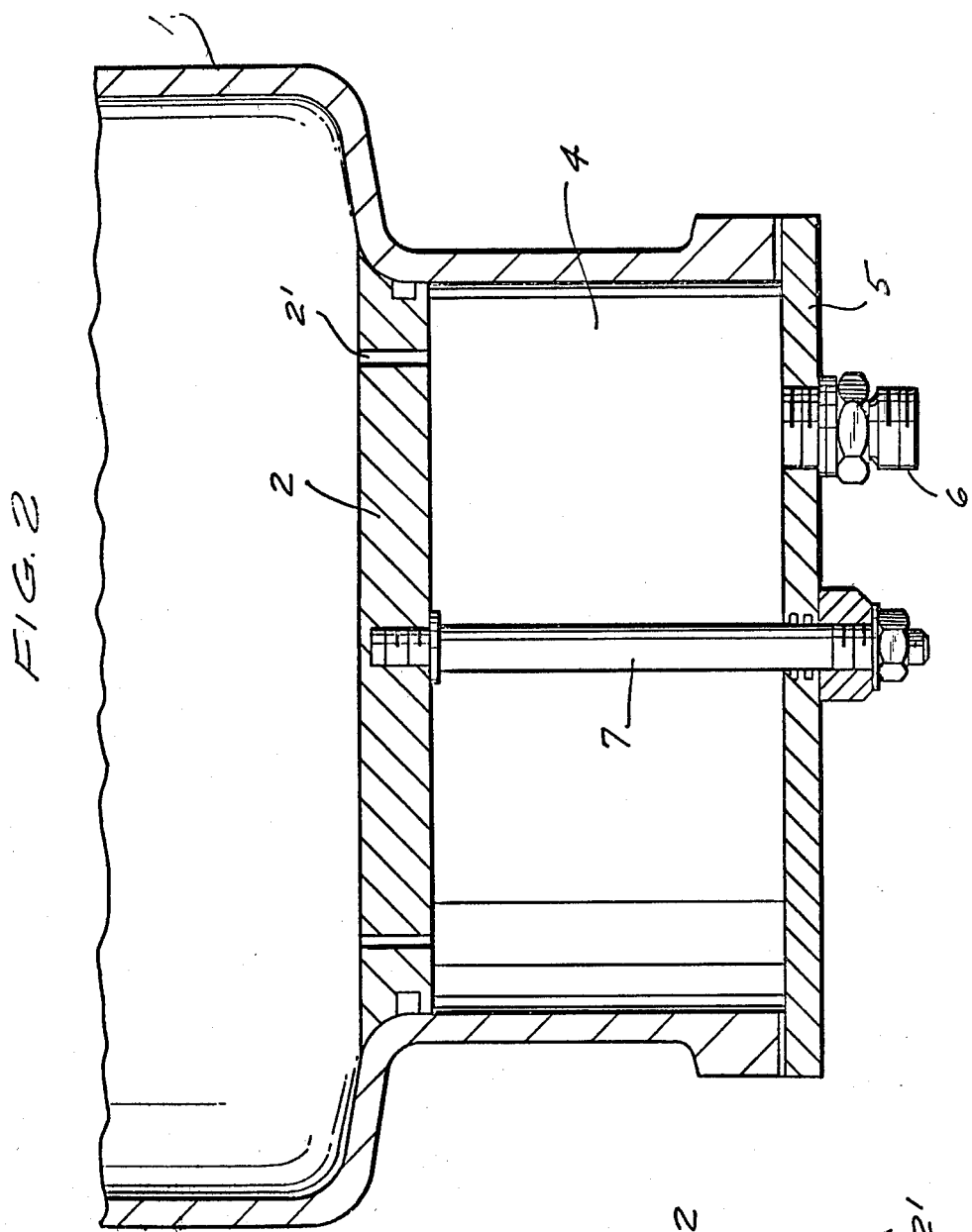
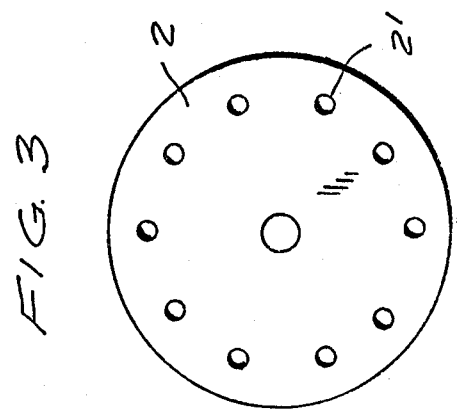

METHOD OF AND AN ARRANGEMENT FOR CULTIVATING CELLS OF ANIMAL AND HUMAN TISSUES

This is a continuation, of application Ser. No. 840,165 now U.S. Pat. No. 4,173,516, filed Oct. 6, 1977 which in turn is a division of application Ser. No. 814,415, filed July 11, 1977 now abandoned.

BACKGROUND OF THE INVENTION

The present invention relates to a method of cultivating cells of animal and human tissues and to an arrangement for performing the method.

Methods of and arrangements for cultivating cells of animal and human tissues have been already proposed in the art. When the cells are to be grown they are introduced into a nutrient solution and maintained in the latter in a suspended state. At the same time, required conditions for growth of the cells are established, such as a predetermined temperature, concentration of oxygen and the like.

If the liquid nutrient solution containing the cells is enclosed in a container and stands immovably therein, the cells have a tendency to settle on bottom and walls of the container inasmuch as their specific weight is greater than that of the nutrient solution. In this case the cells form substantially compact deposits which hinder the diffusion required for supplying the cells with oxygen. Cells which are not sufficiently supplied with oxygen will, of course, perish as is well known.

The above problem has been recognized in the art and methods of cultivating the cells have been proposed, including forcedly moving a suspension of the cells in the the nutrient solution. In such a method the nutrient solution is brought into movement by a mechanical stirrer, magnetic stirrer, vibration mixer or the like. At the same time, oxygen is admitted into the container which encloses the nutrient solution containing the cells. The above method has been proved to be satisfactory when the cultivation of the cells is performed in a substantially small container and with a substantially small quantity of nutrient solution. However, when cultivation of the cells is performed in larger containers and with a greater quantity of the nutrient solution, some difficulties develop.

First of all, working elements of the above stirrers and mixers, such as stirring blades, produce a relatively great shearing force which essentially mechanically damages the cells and thereby impedes the growth of the cells. Further, the large arrangements needed require substantial apparatus expenditures for moving the stirring or mixing working elements. In addition, when a mechanical stirrer is used, a shaft of the stirrer extends through an opening in a wall of the container and lubricating of the shaft, which is necessary for operation, results in difficulties in maintaining the sterility of the contents of the container. Finally, in the case when a great quantity of the nutrient solution is enclosed in a large container, oxygen which is supplied in an oxygen-containing gas produces, in the presence of the moving stirring or mixing elements, an undesirable foam.

SUMMARY OF THE INVENTION

Accordingly, it is an object of the present invention to provide a method of and an arrangement for cultivating of animal and human tissues, which avoid the disadvantages of the prior art methods and arrangements.

More particularly, it is an object of the present invention to provide such a method and an arrangement which do not require use of mechanical means for circulating a nutrient solution containing cells therein, and therefore do not damage the highly sensitive cells.

Another object of the present invention is to provide a method and an arrangement which provide for a uniform and substantially turbulence-free circulation of a nutrient solution containing the cells to be cultivated, over the entire interior space of the container so that the speed of circulatory movement is substantially equal at all points in this space of the container.

Still another feature of the present invention is to provide a method and an arrangement which assure a substantially uniform and sufficient supply of oxygen to all the cells contained in the nutrient solution, without producing an undesirable foam.

A further object of the present invention is to provide an arrangement which requires less apparatus expenditures (i.e., a simpler, less expensive apparatus) than the prior art methods and arrangements.

Still a further object of the present invention is to provide a method and an arrangement which permit cultivating the cells in containers of any large size.

In keeping with these objects, and with others which will become apparent hereinafter, one feature of the present invention is embodied in a method of cultivating cells of animal and human tissues, which comprises the steps of introducing the cells into a nutrient solution in which they tend to settle, and maintaining the cells in the nutrient solution in a suspended state so as to prevent their settling by introducing an oxygen-containing gas into the nutrient solution. An arrangement in accordance with the present invention comprises a container for a nutrient solution containing the cells to be cultivated, means for introducing an oxygen-containing gas into the container so as to prevent the cells from settling and maintaining them in suspended state, and guide means in the container and operative for guiding the nutrient solution in the container so that the solution performs a circulatory movement in the container when the oxygen-containing gas is introduced in the latter.

In the above method and arrangement no mechanical means are used for circulating the nutrient solution and therefore the highly sensitive cells are not damaged. A uniform and substantially turbulence-free circulation of the nutrient solution is provided throughout the entire interior space of the container so that the speed of movement of the nutrient solution is substantially equal in any place of the container (i.e. at any point of its interior). This assures a substantially uniform and sufficient exchange of oxygen in the nutrient solution, and, on the other hand, prevents the producing of a foam. The thus constructed arrangement requires less apparatus expenditures than the prior art. Finally, the cells can be cultivated in containers of any desired large size.

It is advantageous when the oxygen-containing gas is introduced into the container in a form of gas bubbles of a predetermined dimension.

The guide means may be formed as a tubular member located in the container and forming an inner hollow within the tubular member, and the outer hollow between the latter and the container. The guide means may be formed as a substantially flat partition wall which is spaced from the opposite walls of the container and subdivides the latter into two hollows. The container may be formed as a circumferentially complete tubular member whose inner walls serves as the above guide means. The nutrient solution circulates around the guide means in the hollows formed between the latter and the walls of the container.

The gas introducing means may include a bottom plate provided with a plurality of openings. The bottom plate may be formed as a bottom wall of the container and provided with between 2 and 10 openings each of a cross-sectional area equal to substantially between 0.5 and 5.0 millimeters.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

For scale up, it is important to keep the number of holes in a constant relation to the cross sectional area of the draft tube. We have found that the optimal number of openings in the bottom wall of the container have to be between 2 and 5 openings per 100 $cm^2$ of a cross sectional area of the inner diameter of the draft tube.

BRIEF DESCRIPTION OF THE DRAWING

FIG. 2 is an enlarged view of a lower portion of the arrangement of FIG. 1;

FIG. 3 is a view from below of a perforated bottom wall of a container of the arrangement of FIG. 1;

DESCRIPTION OF THE PREFERRED EMBODIMENTS

Figure 1:
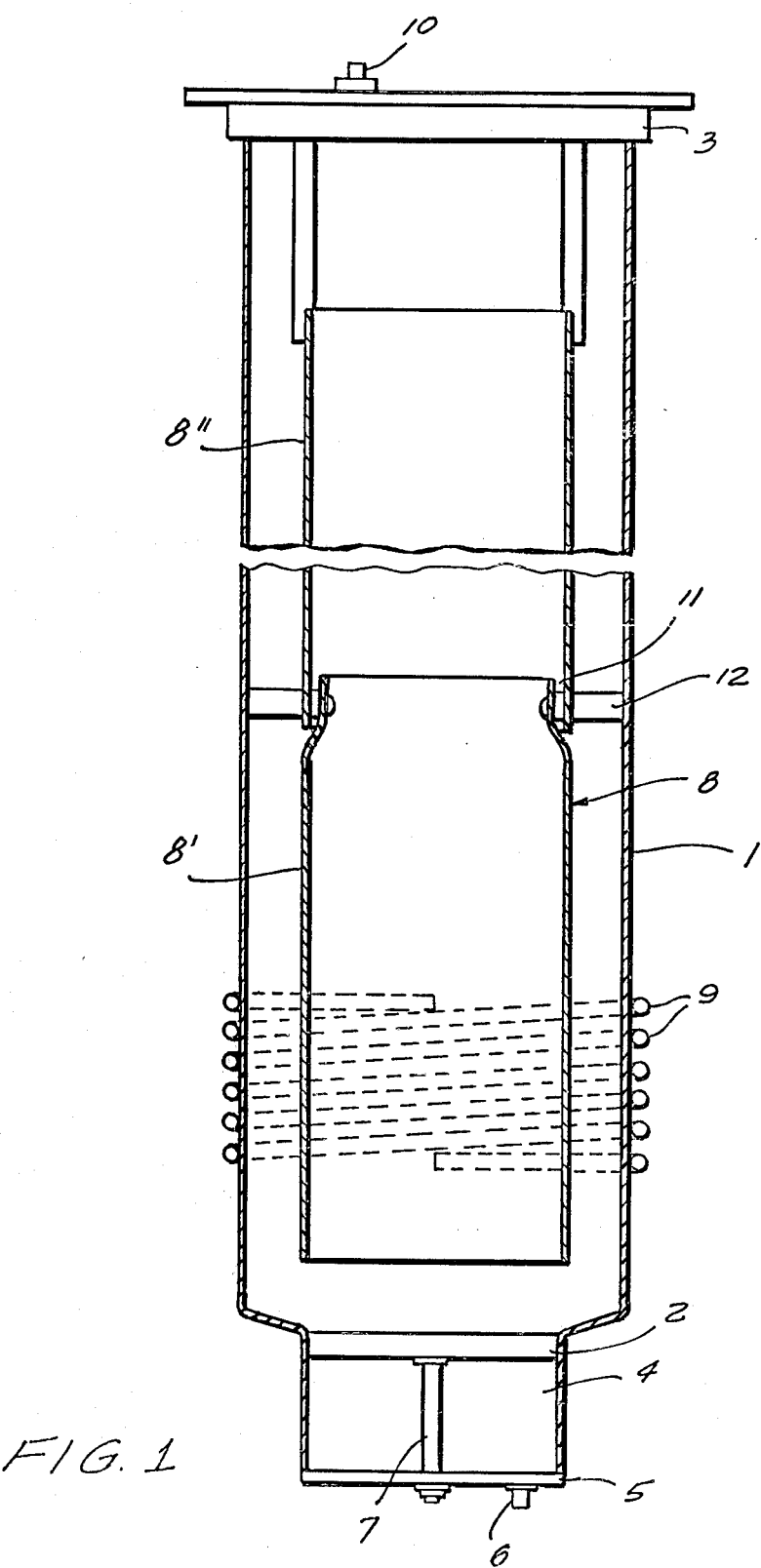
FIG. 1 is a schematic view of an arrangement for cultivating cells of animal and human tissues, in accordance with the present invention.

An arrangement for cultivating cells of animal and human tissues which embodies one form of the present invention, is shown in FIG. 1. The arrangement includes a vertical tubular container 1 of glass or other suitable material. The container is closed from above by a cover 3 and from below by a plate 2 forming a bottom of the container. A chamber 4 is located below the bottom plate 2 of the container 1 and has a transverse cross-section which is less than that of the container 1. The chamber 4 communicates with a not-shown source of a pressurized oxygen-containing gas.

As clearly shown in FIG. 2, the chamber 4 is closed from below by a metal plate 5 which is fixedly connected with the bottom plate 2 of the container 1 by a bolt 7. The metal plate 5 has a bore; and a nipple 6 for connecting the chamber 4 with a gas supply conduit is threaded into this bore. The bottom plate 2 is provided with openings 2' which communicate the chamber 4 with an inner chamber of the container 1.

A tubular member 8 is located within the chamber of the container 1 and spaced from the walls of the latter. The thus located tubular member 8 forms together with the container 1 an inner hollow bounded within the tubular member 8, and an outer hollow bounded between the tubular member 8 and the walls of the container 1. The tubular member 8 forms circulating means for circulating a nutrient medium which contains cells to be cultivated, within and without the tubular member 8. The tubular member 8 is spaced from the walls of the container at such a distance that the cross-sectional area of the inner hollow is substantially equal to the cross-sectional area of the outer hollow. The tubular member 8 supports the cover 3 from above. On the other hand, the tubular member 8 is so located relative to the bottom plate 2 and the walls of the container 1 that the cross-sectional area of a flow which passes between the tubular member 8 and the bottom plate, is substantially equal to that of the flow passing between the tubular member 8 and the walls of the container 1. A heating coil 9 is mounting on the outer side of the wall of the container 1. At least one outlet hole 10 is formed in the cover 3 of the container.

A method of cultivating cells of animal and human tissues as performed with the above arrangement is comprised in the following.

The container 1 is filled with the nutrient solution containing the cells in a suspended state, to a such height that the distance between the level of fluid and the upper end of the tubular member 8 corresponds to the distance between the tubular member 8 and the bottom plate 2 of the container. A gas containing oxygen and carbon dioxide is admitted into the chamber 4 and thereafter issues from the holes 2' of the bottom plate 2 into the chamber of the container 1. The particular composition of the gas is selected in dependence upon the specific requirements made by the cultures to be cultivated. The gas is introduced only at such a pressure which is necessary to overcome the weight of fluid passing through the holes 2' of the bottom plate 2 so as to bring the fluid into circulatory movement. The admitted oxygen-containing gas is divided by the fluid passing through the holes 2' of the bottom plate 2 into large bubbles of substantially equal dimensions. The bubbles move up in the inner hollow of the tubular member 8 under the action of the continuously supplied oxygen-containing gas and cause the desired circulation of the nutrient solution. Due to the specific construction and location of the tubular member 8 the nutrient solution performs a circulatory movement from the inner hollow of the tubular member 8 into the outer hollow formed between the tubular member 8 and the walls of the container 1.

As shown in FIG. 3, ten openings 2' are provided in the bottom plate 2 of the container. The openings 2' are arranged in a circle which is located within a projection of the outer periphery of the tubular member 8 on the bottom plate 2. The quantity and the dimensions of the openings 2' are selected together with the predetermined gas pressure, in accordance with the desired dimension of the gas bubbles or the quantity of the introduced gas. There may be provided from two to ten such openings, preferably four of them. The cross-sectional area of the openings 2' may be substantially between 0.5 and 5.0 millimeters, preferably 1.5 millimeters.

The container 1, the chamber 4 and the tubular member 8 may be of a cylindrical cross-section. However, it is understood that they may be also of any other cross-section. As shown in FIG. 1, the tubular member 8 consists of two tubular portions 8' and 8". The tubular portions 8' and 8" form therebetween an annular opening 11 and are connected with each other by a web 12 which serves also to position the portions in a spaced relationship with the walls of the container 1. Such construction permits, in the case when a batch is changed, to draw off a portion, for instance a half of the culture or the nutrient solution, and thereby to provide for the operation of the arrangement at a reduced filling level of the container.

The above arrangement within the ambit of the invention may be of a construction different from that of described above. Thus, the bottom plate 2 may be ring-shaped and so located that the flow of the nutrient solution moves upwardly in the outer hollow between the tubular member 8 and the walls of the container 1, so as to provide an inverted circulatory movement.

Figure 4:
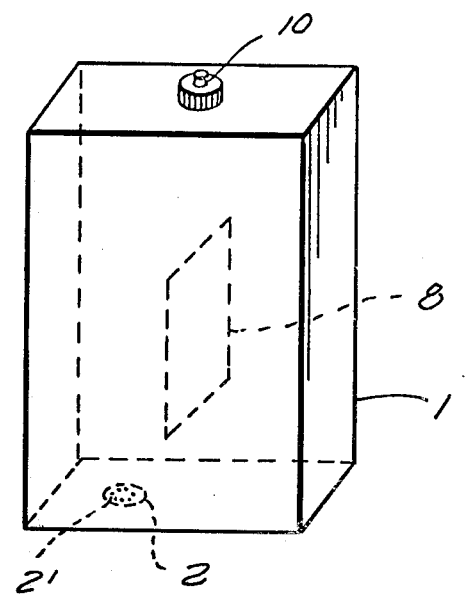
FIG. 4 is a schematic view of an arrangement in accordance with a further embodiment of the present invention.

The bottom plate may be located eccentrically relative to the container 1, and the member 8 may be formed as a substantially flat partition wall, as shown in FIG. 4, which partition wall is spaced at a distance from the walls of the container 1.

Figure 5:
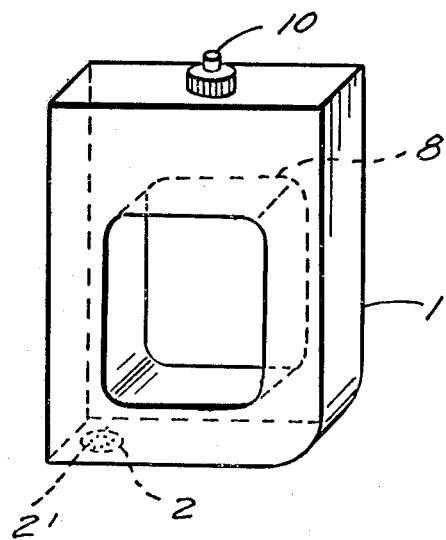
FIG. 5 is a schematic view of an arrangement in accordance with a still further embodiment of the present invention.

Still another ambodiment of the present invention is shown in FIG. 5. Here, the container 1 is formed as a circumferentially closed tubular member 1 whose inner wall forms the member 8. The nutrient solution circulates in a space between the inner and the outer walls of the thus formed container 1. The bottom plate 2 is eccentrically displaced relative to the container 1 so that the openings 2' are open at a vertical tubular portion of the tubular container 1.

The arrangements shown in FIGS. 4 and 5 operate in the same manner as that shown in FIG. 1.

Figure 6:
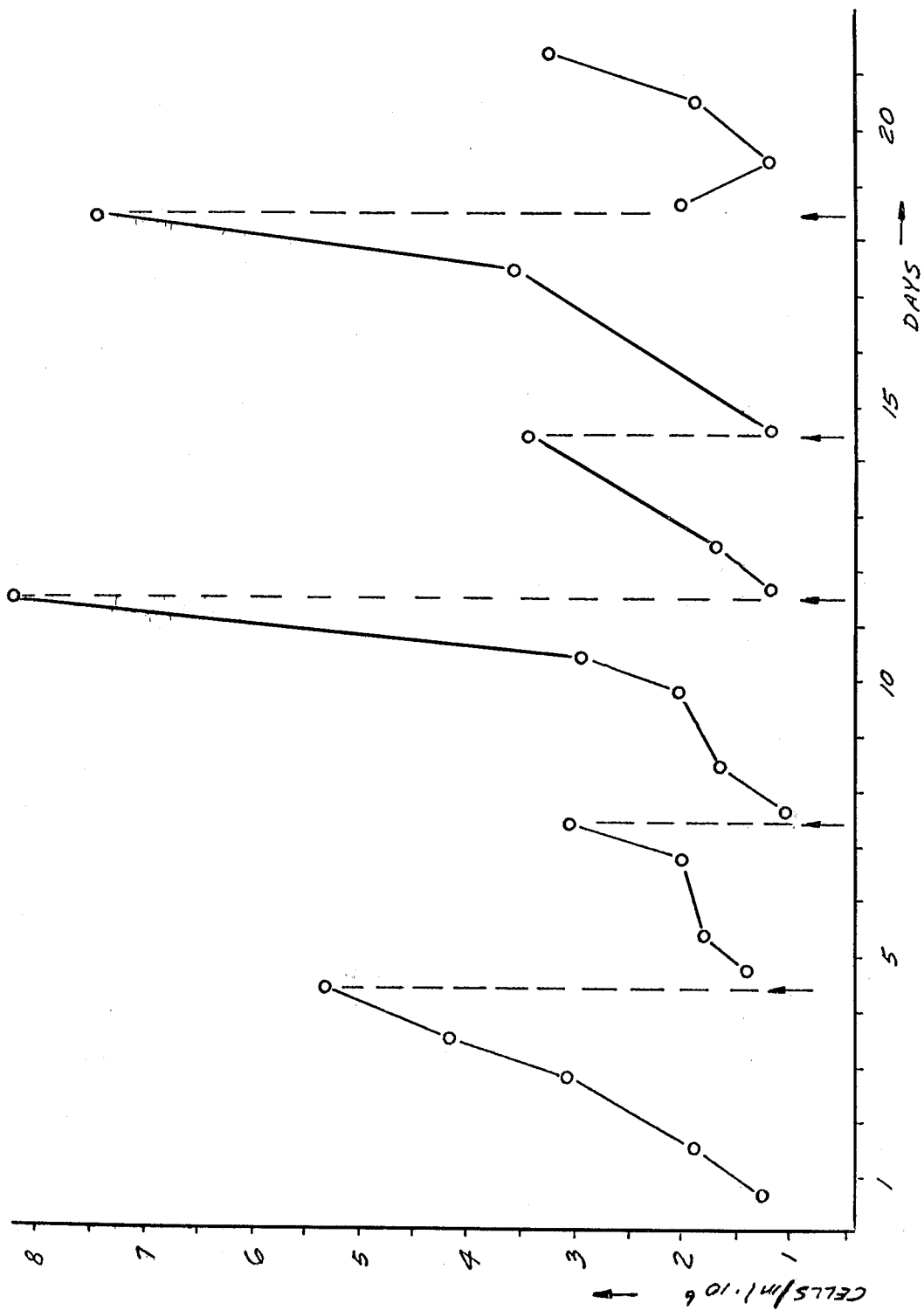
FIG. 6 is a diagram illustrating an operation of the arrangement, in accordance with the invention.

FIG. 6 shows a diagram which illustrates the operation of the arrangement of FIGS. 1 and 2. The portions of curves which join circles with each other indicate a growth rate of the cells, such as lymphoblastic cells, whereas the arrows indicate a removal of the cell culture.

It will be understood that each of the elements described above, or two or more together, may also find a useful application in other types of construction differing from the types described above.

While the invention has been illustrated and described as embodied in a method of and an arrangement for cultivating cells of animal and human tissues, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for cultivating cells of animal and human tissues which are highly susceptible to damage resulting from agitation, comprising an upright container which bounds an unobstructed inner chamber for nutrient solution containing the cells which tend to settle in the solution; guide means located in said inner chamber of said container and subdividing the interior of the latter into two unobstructed zones; means for accommodating an oxygen-containing gas and including an outer gas chamber located below said container; and means for introducing said oxygen-containing gas from said outer gas chamber of said accommodating means into said inner chamber of said container, said introducing means including a plate separating said outer gas chamber from said inner chamber of said container and having a plurality of outlet openings communicating said outer gas chamber with said inner chamber so as to introduce said oxygen-containing gas from the former into the latter, wherein the number and the dimensions of said outlet openings are such that when said oxygen-containing gas is introduced from said outer gas chamber into said inner chamber of said container through said plurality of outlet openings of said plate, it imparts to said nutrient solution in said inner chamber a circulatory movement between said unobstructed zones which is sufficient to prevent the cells from settling and maintain them in suspended state, but is so slight as to avoid agitating said nutrient solution with concomitant damage to the cells, said introducing means constituting the only means for imparting circulatory movement to said nutrient solution and maintaining the cells in suspended state.

2. The arrangement as defined in claim 1, wherein said plate is horizontal.

3. The arrangement as defined in claim 1, wherein said container has side walls, and said guide means is a tubular member located within said container and inwardly spaced from said side walls thereof, so as to form an inner hollow inside said tubular member defining one of said zones and an outer hollow between said tubular member and the walls of said container defining the other of said zones, for circulating said nutrient solution therethrough.

4. The arrangement as defined in claim 3, wherein said container and said tubular member are cylindrical.

5. The arrangement as defined in claim 3, wherein said tubular member is spaced from said walls of said container at a predetermined distance so that a cross-section of a flow of said nutrient solution circulating in said inner hollow is substantially equal to that of circulating in said outer hollow.

6. The arrangement as defined in claim 3, wherein said outlet openings being located within a projection of an outer circumference of said tubular member on said element.

7. The arrangement as defined in claim 6, wherein said container has a bottom wall forming said plate.

8. The arrangement as defined in claim 3, wherein said tubular member is so located relative to said plate and to said side walls of said container that the cross-sectional area of the flow of the nutrient solution which passes between said tubular member and said plate is substantially equal to that of the flow of the nutrient solution which passes between said tubular member and said walls of said container.

9. The arrangement as defined in claim 1, wherein said plate has between 2 and 10 outlet openings, for each 200 square centimeters of the cross sectional area of said draft tube.

10. The arrangement as defined in claim 9, wherein said plate has four outlet openings for between 100 and 200 square centimeters of said cross sectional area of said draft tube.

11. The arrangement as defined in claim 1, wherein each of said outlet openings has a cross-sectional area equal to substantially between 0.5 and 5 millimeters.

12. The arrangement as defined in claim 11, wherein each of said outlet openings has a cross-sectional area equal to 1.5 millimeter.

13. The arrangement as defined in claim 1, wherein said container has side walls, and said guide means is a partition wall located within said container and spaced from the opposite walls thereof so as to form two hollows each between said partition wall and the respective wall of said container and defining said two zones, respectively, for circulating said nutrient solution therethrough.

14. The arrangement as defined in claim 1, wherein said container is formed as a circumferentially complete tubular member having an inner wall which forms said guiding means.

15. The arrangement as defined in claim 14, wherein said tubular member has a vertical axial plane and at least one vertical tubular portion, said outlet openings being displaced relative to said vertical axial plane of said container so that they face towards said vertical tubular portions of said tubular member.

16. The arrangement as defined in claim 1, wherein said container has two spaced end portions and said guide means have two further end portions each adjacent to the respective end portion of said container, said plate being located at a region adjacent to one of said further end portions of said guide means.

* * * * *